US006287582B1

(12) United States Patent
Gott et al.

(10) Patent No.: US 6,287,582 B1
(45) Date of Patent: Sep. 11, 2001

(54) TOWELETTE PRODUCT

(75) Inventors: Robert Edward Gott, Norwalk; Craig Stephen Slavtcheff, Guilford; Alexander Paul Znaiden, Trumbull, all of CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/563,252

(22) Filed: May 1, 2000

Related U.S. Application Data
(60) Provisional application No. 60/150,481, filed on Aug. 24, 1999.

(51) Int. Cl.[7] .................................................. A01N 25/34
(52) U.S. Cl. ......................... 424/402; 424/400; 424/401; 424/404
(58) Field of Search ..................... 424/401, 402, 424/404, 443, 65, 66, 67, 68; 514/828

(56) References Cited

U.S. PATENT DOCUMENTS

| | | | |
|---|---|---|---|
| 3,856,941 | * 12/1974 | Turner ................................... | 424/642 |
| 4,128,631 | * 12/1978 | Lundmark et al. ..................... | 424/70 |
| 4,762,847 | * 8/1988 | Edwards et al. ....................... | 514/336 |
| 4,764,418 | 8/1988 | Kuenn et al. . | |
| 4,828,912 | 5/1989 | Hossain et al. . | |
| 4,941,995 | 7/1990 | Richards . | |
| 5,091,171 | 2/1992 | Yu et al. . | |
| 5,403,588 | * 4/1995 | Santa Ana, Jr. ....................... | 424/402 |
| 5,505,948 | 4/1996 | Rapaport . | |
| 5,534,265 | 7/1996 | Fowler et al. . | |
| 5,567,427 | * 10/1996 | Papadakis ............................. | 424/401 |
| 5,620,694 | 4/1997 | Giardot . | |
| 5,648,083 | 7/1997 | Blieszner et al. . | |
| 5,720,961 | 2/1998 | Fowler et al. . | |
| 5,730,991 | 3/1998 | Rapaport . | |
| 5,744,149 | 4/1998 | Giardot . | |
| 5,756,112 | 5/1998 | Mackey . | |
| 5,776,473 | 7/1998 | Perricone et al. . | |
| 5,869,172 | 2/1999 | Caldwell . | |
| 5,958,436 | 9/1999 | Hahn et al. . | |
| 5,965,616 | 10/1999 | Wang et al. . | |
| 5,976,565 | 11/1999 | Fotinos . | |
| 5,980,924 | 11/1999 | Yamazaki et al. . | |
| 5,985,300 | 11/1999 | Crotty et al. . | |
| 5,993,832 | 11/1999 | Lorant et al. . | |
| 6,063,390 | * 5/2000 | Farrell et al. ......................... | 424/404 |
| 6,063,397 | 5/2000 | Fowler et al. . | |
| 6,106,818 | 8/2000 | Dulog et al. . | |
| 6,110,205 | 8/2000 | Nies . | |

FOREIGN PATENT DOCUMENTS

| | | |
|---|---|---|
| 96/11572 | 4/1996 | (WO) . |
| 00/61083 | 10/2000 | (WO) . |
| 00/61105 | 10/2000 | (WO) . |
| 00/61106 | 10/2000 | (WO) . |
| 00/61107 | 10/2000 | (WO) . |

* cited by examiner

*Primary Examiner*—Thurman K. Page
*Assistant Examiner*—Charesse L. Evans
(74) *Attorney, Agent, or Firm*—Milton L. Honig

(57) ABSTRACT

A disposable towelette product is provided which includes a flexible water-insoluble substrate such as a tissue impregnated with an alpha- or beta-hydroxycarboxylic acid in a cosmetically acceptable carrier vehicle. Impregnated cosmetic composition in water will have a pH no higher than 6.8. A silicone microemulsion is present to minimize any stickiness resulting from deposition of the hydroxycarboxylic acid by the towelette onto the skin. In the presence of fatty acid group containing surfactants, the silicone microemulsion controls foul odors that the surfactants may emit through hydrolysis at low pH.

15 Claims, No Drawings

TOWELETTE PRODUCT

BACKGROUND OF THE INVENTION

This application claims benefit of provisional application Ser. No. 60/150,481 filed Aug. 24, 1999.

FIELD OF THE INVENTION

The invention concerns single use towelettes for cosmetically delivering alpha-hydroxycarboxylic acids.

THE RELATED ART

Alpha-hydroxycarboxylic acids and their derivatives have widely been advertised as treatment for maintaining a youthful look. These substances are said to control development of facial fine lines and wrinkles. Formulation of these substances have been difficult. Among the problems have been compatibility with carrier systems, physical stability and skin irritation. Particularly difficult to formulate are low pH systems.

U.S. Pat. No. 5,091,171 (Yu et al.) was one of the first documents describing the use of alpha-hydroxycarboxylic acids as being effective against the appearance of fine lines and wrinkles. Subsequent thereto a vast literature and many commercial products were generated based on the efficacy of these materials. Most often the formulations were of the cream or lotion type. One problem with these formulations is that they do not always evenly distribute over the applied surfaces. Secondly, any time an active treated surface is followed by a cleansing, the active washes away. Methods to maintain alpha-hydroxycarboxylic acids on a skin surface are needed which are not as susceptible to subsequent cleansing actions. Irritation has also been of great concern because the formulations are generally of low pH.

WO 96/11572 (Moberg) has utilized a variety of acids including the alpha-hydroxy substance known as lactic acid in an aqueous hexylene glycol formula impregnated onto textiles or refreshing napkins. These were employed to overcome the problem of microbial growth on skin and served as a disinfection treatment.

U.S. Pat. No. 4,828,912 (Hossain et al.) and U.S. Pat. No. 4,764,418 (Kuenn et al.) describe virucidal tissue products directed at controlling disease inducing organisms such as viruses and the common cold. Carboxylic acids such as citric, malic, succinic and benzoic acids are formulated with surfactants and a carrier for impregnation into facial tissues or other non-woven materials.

None of the above disclosures have been concerned with the issue of stickiness of the alpha-hydroxycarboxylic acids once they have been deposited by the towelette onto the skin. Neither has there been any discussion with respect to odor control which may arise in low pH systems.

Accordingly, it is an object of the present invention to provide a product and method for both cleansing skin and reducing the signs of aging.

Another object of the present invention is to provide a product and method which deposited alpha-hydroxycarboxylic acids in a manner that avoids formation of sticky residues on the skin.

Still another object of the present invention is to provide a product delivering alpha-hydroxycarboxylic acids in a formulation that avoids formation of foul odors.

These and other objects of the present invention will become more apparent from the following summary and detailed discussion which follow.

SUMMARY OF THE INVENTION

A towelette product is provided which includes:
(a) a water-insoluble substrate;
(b) a cosmetic composition impregnated into the substrate including:
  (i) an alpha or beta-hydroxycarboxylic acid;
  (ii) a silicone microemulsion;
  (iii) the composition in water having a pH no higher than about 6.5.

Silicone microemulsions of the present invention operate to provide both stability to the composition and counteract any stickiness which may occur when the alpha-hydroxycarboxylic acids are deposited onto the skin.

Surfactants, especially mild surfactants such as those of the amphoteric type may in the presence of low pH decompose thereby emitting foul odors. Silicone microemulsions of the present invention have also found youthfulness in counteracting generation of the foul odors.

DETAILED DESCRIPTION OF THE INVENTION

Now it has been found that towelettes impregnated with alpha-hydroxycarboxylic acids can be delivered to the skin without imparting any stickiness. Silicone microemulsions solve this problem. Normally creams, lotions and other types of cosmetic vehicles containing the alpha-hydroxycarboxylic acids contain emollients. For instance these emollients may be esters, hydrocarbons or dimethicone oils. These emollients deposit on the skin along with the actives. The presence of the emollients obscures any stickiness which may result from water or carrier evaporation leaving dried active behind. Unfortunately towelette products cannot be impregnated with fluids of too high viscosity. Towelettes will not adequately wet out where the fluid to be impregnated is too thick. Low viscosity fluids which must be used with towelettes are susceptible to poor emulsion stability. Large amounts of emollients are difficult to formulate into these systems. Consequently, actives such as alpha-hydroxycarboxylic acids deposit in a sticky manner onto skin from the low viscosity fluids spread thereon by the towelettes.

A first necessary aspect of the present invention is that of a substrate. Preferably the substrate is a water insoluble substance. By "water insoluble" is meant the substrate does not dissolve in or readily break apart upon immersion in water. Another advantage of the substrate in combination with the active is that the former helps the active penetrate. The substrate is also much better than a mere liquid or gel formulation in the accurate application to the skin and avoidance of sensitive areas such as inadvertently directing the astringent composition to areas of the eye thereby irritating same.

A wide variety of materials can be used as the substrate. The following nonlimiting characteristics are desirable: (I) sufficient wet strength for use, (ii) sufficient abrasivity, (iii) sufficient loft and porosity, (iv) sufficient thickness, (v) appropriate size, and (vi) non-reactive with components of the impregnating composition.

Nonlimiting examples of suitable substrates which meet the above criteria include nonwoven substrates, woven substrates, hydroentangled substrates, air entangled substrates and the like. Preferred embodiments employ nonwoven substrates since they are economical and readily available in a variety of materials. By nonwoven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof. Wood pulp fibers are preferred while all cotton fibers (e.g. cotton pads) are normally avoided.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele®; polyamides such as Nylons (e.g., Nylon 6, Nylon 66, Nylon 610 and the like); polyesters such as Fortrel®, Kodel®, and the polyethylene terephthalate fibers, Dacron®; polyolefins such as polypropylene, polyethylene; polyvinyl acetate fibers and mixtures thereof.

Nonwoven substrates made from natural materials consist of webs or sheets most commonly formed on a fine wire screen from a liquid suspension of the fibers.

Substrates made from natural materials useful in the present invention can be obtained from a wide variety of commercial sources. Nonlimiting examples of suitable commercially available paper layers useful herein include Airtex®, an embossed airlaid cellulosic layer having a base weight of about 71 gsy, available from James River Corporation, Green Bay, Wis.; and Walkisoft®, an embossed airlaid cellulosic having a base weight of about 75 gsy, available from Walkisoft U.S.A., Mount Holly, N.C.

Nonwoven substrates made from synthetic materials useful in the present invention can also be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 43 grams per square yard (gsy), available from Veratec, Inc., Walpole, Mass.; HEF 140-102, an apertured hydroentangled material containing about 50% rayon and 50% polyester, and having a basis weight of about 56 gsy, available from Veratec, Inc., Walpole, Mass.; Novenet® 149-191, a thermo-bonded grid patterned material containing about 69% rayon, about 25% polypropylene, and about 6% cotton, and having a basis weight of about 100 gsy, available from Veratec, Inc., Walpole, Mass.; HEF Nubtex® 149-801, a nubbed, apertured hydroentangled material, containing about 100% polyester, and having a basis weight of about 70 gsy, available from Veratec, Inc. Walpole, Mass.; Keybak® 951V, a dry formed apertured material, containing about 75% rayon, about 25% acrylic fibers, and having a basis weight of about 43 gsy, available from Chicopee Corporation, New Brunswick, N.J.; Keybak® 1368, an apertured material, containing about 75% rayon, about 5% polyester, and having a basis weight of about 39 gsy, available from Chicopee Corporation, New Brunswick, N.J.; Duralace® 1236, an apertured, hydroentangled material, containing about 100% rayon, and having a basis weight from about 40 gsy to about 115 gsy, available from Chicopee Corporation, New Brunswick, N.J.; Duralace® 5904, an apertured, hydroentangled material, containing about 100% polyester, and having a basis weight from about 40 gsy to about 115 gsy, available from Chicopee Corporation, New Brunswick, N.J.; Sontaro® 8868, a hydroentangled material, containing about 50% cellulose and about 50% polyester, and having a basis weight of about 60 gsy, available from Dupont Chemical Corp.

Most preferred as a towelette for purposes of this invention are non-woven substrates, especially blends of rayon/polyester and ratios of 10:90 to 90:10, preferably ratios of 20:80 to 80:20, optimally 40:60 to 60:40 by weight. A most useful towelette is a 70:30 rayon/polyester non-woven wipe article.

The substrate can be made into a wide variety of shapes and forms. Generally the substrate is in single use towelette form. Advantageously, the towelettes are folded in a Z-shaped formation. They may be interleaved with one another but preferably are not interleaved. The Z fold consists of a center panel flanked by upper and lower wing panels. The upper and lower wing panels are substantially of equal width and substantially half of a width of the center panel. Each towelette is folded medially in a direction orthogonal to that of the Z-shaped formation. Advantageously the size of the towelette may range in length from 10 to 40 cm, preferably from 15 to 30 cm, optimally from 18 to 24 cm. The width of the towelette may range from 8 to 30 cm, preferably from 10 to 25 cm, optimally from 15 to 20 cm.

Anywhere from 5 to 100, preferably from 10 to 50 single towelettes may be stored within a dispensing pouch, preferably a moisture impermeable pouch. During storage and between dispensing, the pouch is resealable, usually via an adhesive strip covering a dispensing opening. Single towelette containing pouches may also be employed.

The substrates of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different colors, thereby helping the user to further distinguish the surfaces.

A second important element of the present invention is that of an alpha-hydroxycarboxylic acid. By this term is meant not only the acid form but also salts thereof. Typical cationic counterions to form the salt are the alkali metals, alkaline earth metals, ammonium, $C_2$–$C_8$ trialkanolammonium cation and mixtures thereof. The term "alpha-hydroxycarboxylic acids" include not only hydroxyacids but also alpha-ketoacids and related compounds of polymeric forms of hydroxyacid.

Hydroxyacids are organic carboxylic acids in which one hydroxyl group is attached to the alpha carbon adjacent the carboxy group. The generic structure is as follows:

(Ra)(Rb)C(OH)COOH where Ra and Rb are H, F, Cl, Br, alkyl, aralkyl or aryl group of saturated or unsaturated, isomeric or non-isomeric, straight or branched chain or cyclic form, having 1 to 25 carbon atoms, and in addition Ra and Rb may carry OH, CHO, COOH and alkoxy groups having 1 to 9 carbon atoms. The alpha-hydroxyacids may be present as a free acid or in lactone form, or in a salt form with an organic base or an inorganic alkali. The alpha-hydroxyacids may exist as stereoisomers as D, L, and DL forms when Ra and Rb are not identical.

Typical alkyl, aralkyl and aryl groups for Ra and Rb include methyl, ethyl, propyl, isopropyl, butyl, pentyl, octyl, lauryl, stearyl, benzyl and phenyl, etc. The alpha-hydroxyacids of the first group may be sub-divided into (1) alkyl alpha-hydroxyacids, (2) aralkyl and aryl alpha-hydroxyacids, (3) polyhydroxy alpha-hydroxyacids, and (4) polycarboxylic alpha-hydroxyacids. The following are representative alpha hydroxyacids in each subgroup.

(1) Alkyl Alpha Hydroxyacids
    2-Hydroxyethancic acid (Glycolic acid, hydroxyacetic acid)
    2-Hydroxypropanoic acid (Lactic acid)
    2-Methyl 2-hydroxypropanoic acid (Methyllactic acid)
    2-Hydroxybutanoic acid
    2-Hydroxypentanoic acid
    2-Hydroxyhexanoic acid
    2-Hydroxyheptanoic acid
    2-Hydroxyoctanoic acid
    2-Hyroxynonanoic acid
    2-Hydroxydecanoic acid
    2-hydroxyundecanoic acid
    2-Hydroxydodecanoic acid (Alpha hydroxylauric acid)
    2-Hydroxytetradecanoic acid (Alpha hydroxymyristic acid)
    2-Hydroxyhexadecanoic acid (Alpha hydroxypalmitic acid)
    2-Hydroxyoctadecanoic acid (Alpha hydroxystearic acid)
    2-Hydroxyeicosanoic acid (Alpha hydroxyarachidonic acid)

(2) Aralkyl And Aryl Alpha-Hydroxyacids
    2-Phenyl 2-hydroxyethanoic acid (Mandelic acid)
    2,2-Diphenyl 2-hydroxyethanoic acid (Benzilic acid)
    3-Phenyl 2-hydroxypropanoic acid (Phenyllactic acid)
    2-Phenyl 2-methyl 2-hydroxyethanoic acid (Atrolactic acid)
    2-(4'-Hydroxyphenyl) 2-hydroxyethanoic acid (4-Hydroxymandelic acid)
    2-(4'-Chlorophenyl) 2-hydroxyethanoic acid (4-Chloromandelic acid)
    2-(3'-Hydroxy4'-methoxyphenyl) 2-hydroxyethanoic acid (3-Hydroxy-4-methoxymandelic acid)
    2-(4'-Hydroxy-3'-methoxyphenyl acid)
    3-(2'-Hydroxyphenyl) 2-hydroxypropanoic acid [3(2'Hydroxyphenyl) lactic acid]
    3-(4'-Hydroxyphenyl) 2-hydroxypropanoic acid [3-(4'-Hydroxyphenyl) lactic acid]
    2-(3',4'-Dihydroxyphenyl) 2-hydroxyethanoic acid (3,4Dihydroxymandelic acid)

(3) Polyhydroxy Alpha-Hydroxyacids
    2,3-Dihydroxypropanoic acid (Glyceric acid)
    2,3,4-Trihydroxybutanoic acid, Isomers; erythronic acid, threonic acid)
    2,3,4,5-Tetrahydroxypentanoic acid (Isomers; ribonic acid, arabinoic acid, xylonic acid, lyxonic acid)
    2,3,4,5,6-Pentahydroxyhexanic acid (Isomers; allonic acid, altronic acid, gluconic acid, mannoic acid, gulonic acid, idonic acid, galatconic acid, talonic acid)
    2,3,4,5,6,7-Hexahydroxyheptanoic acid (Isomers; glucoheptonic acid, galactoheptonic acid etc.)

(4) Polycarboxylic Alpha-Hydroxyacids
    2-Hydroxypropane-1,3-dioic acid (Tartronic acid)
    2-Hydroxybutane,1,4dioic acid (Malic acid)
    2,3-Dihydroxybutane-1,4dioic acid (Tartaric acid)
    2-Hydroxy-2-carboxypentane,1-5-dioic acid (Citric acid)
    2,3,4,5-Tetrahydroxyhexane,1–5,dioic acid (Isomers: saccharic acid, mucic acid)

(5) Lactone Forms
The typical lactone forms are gluconolactone, galactonolactone, glucuronolactone, glacturonolactone, gluconolactone, ribonolactone, saccharic acid lactone, pantoyllactone, glucoheptonolactone, mannonolactone, and galactoheptonolactone.

Representative alpha ketoacids useful for the present invention are as follows.
    2-Ketoethanoic acid (Glyoxylic acid)
    Methyl 2-ketoethanoate
    2-Ketopropanoic acid (Pyruvic acid)
    Methyl 2-ketopropanoate (Methyl pyruvate)
    Ethyl 2-ketopropanoate (Ethyl pyruvate)
    Propyl 2ketopropanoate (Propyl pyruvate)
    2-Phenyl-2-ketoethanoic acid (Benzoylformic acid)
    Methyl 2-phenyl-2-ketoethanoate (Methyl benzoylformate)
    Ethyl 2-phenyl-2-ketoethanoate (Ethyl benzoylformate)
    3-Phenyl-2-ketopropanoic acid (Phenylpyruvic acid)
    Methyl 3-phenyl-2-ketopropanoate (Methyl phenylpyruvate)
    Ethyl 3-phenyl-2-ketopropanoate (Ethyl phenylpyruvate)
    2-Ketobutanoic acid
    2-Ketopentanoic acid
    2-Ketohexanoic acid
    2-Ketoheptanoic acid
    2-Ketooctanoic acid
    2-Ketododecanoic acid
    Methyl 2-ketooctanoate II. Dimeric and Polymeric Forms of Hydroxyacids When two or more molecules of hydroxycarboxylic acids either identical or non-identical compounds are reacted chemically to each other, dimeric or polymeric compounds will be formed. Such dimeric and polymeric compounds may be classified into three groups, namely (a) acyclic ester, (b) cyclic ester and (c) miscellaneous dimer and polymer.

Representative acylic esters of hydroxycarboxylic acids useful for the present invention are those found below.
    Glycolyl glycollate (Glycolic acid glycollate)
    Lactyl lactate (Lactic acid lactate)
    Mandelyl mandellate Atrolactyl atrolactate
Phenyllactyl phenyllactate
Benzilyl benzillate
Glycolyl lactate
Lactyl glycollate
Glycolyl glycolyl glycollate
Lactyl lactyl lactate
Lactyl glycolyl lactate
Glycolyl glycolyl glycolyl glycollate
Lactyl lactyl lactyl lactate
Glycolyl lactyl glycolyl lactyl glycollate
Polyglycolic acid and polylactic acid Amounts of the alpha-hydroxycarboxylic acids may range from about 0.01 to about 20%, preferably from about 0.1 to about 15%, more preferably from about 1 to about 10%, optimally from about 3 to about 8% by weight of the composition which impregnates the substrate.

Compositions of the present invention when placed in water will have a pH no higher than about 6.5, preferably from about 6.0 to about 2.0, more preferably from about 5.5 to about 2.5, even more preferably from about 5.0 to about 3.0, optimally from about 4.5 to about 3.5. The compositions may be placed on the towelettes in a dry state and activated by a consumer through moistening with water. Yet more preferably compositions of the present invention are pre-prepared fluid compositions of low viscosity. Typical viscosities may range from 0.5 to 100 cps, preferably from about 2 to about 20 cps at 20° C. (Brookfield RVT).

The amount of impregnating composition relative to the substrate may range from about 20:1 to 1:20, preferably from 10:1 to about 1:10 and optimally from about 2:1 to about 1:2 by weight.

A humectant ordinarily is incorporated with compositions of the present invention. Humectants are normally polyols. Representative polyols include glycerin, diglycerin, polyalkylene glycols and more preferably alkylene polyols and their derivatives including propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, isoprene glycol, ethoxylated glycerol, propoxylated glycerol and mixtures thereof. The most preferred is 2-methyl-1,3-propanediol available as MP Diol from the Arco Chemical Company. Amounts of the polyol may range from about 0.5 to about 95%, preferably from about 1 to about 50%, more preferably from about 1.5 to 20%, optimally from about 3 to about 10% by weight of the impregnating composition.

An essential further element of product according to the present invention is that of a silicone microemulsion. Average particle size of the silicone material in these microemulsions may range from about 0.01 nm to about 500 nm, preferably from about 1 to about 100 nm, optimally from about 5 to about 50 nm. Particle size may be measured by means of a laser light scattering technique, using a 2600 D Particle Sizer from Malvern Instruments.

The microemulsions may be prepared by high shear mechanical mixing of the silicone and water, or by emulsifying the insoluble, non-volatile silicone with water and an emulsifier-mixing the silicone into a heated solution of the emulsifier for instance, or by a combination of mechanical and chemical emulsification.

Any surfactant materials either alone or in admixture may be used as emulsifiers in the preparation of the silicone emulsions. Preferred emulsifiers include anionic emulsifiers such as alkylarylsulphonates, e.g. sodium dodecylbenzene sulphonate, alkyl sulphates e.g. sodium, lauryl sulphate, alkyl ether sulphates e.g. sodium lauryl ether sulphate nEO, where n is from 1 to 20 alkylphenol ether sulphates e.g. octylphenol ether sulphate nEO where n is from 1 to 20, and sulphosuccinates e.g. sodium dioctysulphosuccinate.

Also suitable are nonionic emulsifiers such as alkylphenol ethoxylates e.g. nonylphenol ethoxylate nEO, where n is from 1 to 50, alcohol ethoxylates e.g. lauryl alcohol nEO, where n is from 1 to 50, ester ethoxylates e.g. polyoxyethylene monostearate where the number of oxyethylene units is from 1 to 30.

Silicones which are particularly preferred for purposes of this invention are dimethiconols, these may be linear or branched. Average number molecular weight may range from about 1,000 to about 1 million, preferably from about 20,000 to about 500,000, optimally from about 40,000 to about 100,000. Microemulsions may be loaded with the silicone at levels ranging from about 1 to about 95%, preferably from about 10 to about 60%, optimally from about 20 to about 40% by weight. Pre-formed microemulsions are available from suppliers such as Dow Corning, General Electric, Union Carbide, Wacker Chemie, Shin Etsu, and Toray Silicone Company. Particularly preferred is a linear dimethiconyl microemulsion at 25% silicone with a maximum particle size of 40 nm, pH 6.5–8 and surfactant combination of dodecylbenzene sulphonic acid triethanolamine/Laureth-24 available from Dow Corning under the trademark DC 2-1870.

Compositions of this invention when in the form of a fluid will usually be provided with a variety of cosmetically acceptable carrier vehicles. Normally the carrier vehicle will be water. Amounts of the carrier vehicle may range from about 0.5 to about 99%, preferably from about 1 to about 80%, more preferably from about 50 to about 70%, optimally from about 65 to 75% by weight of the impregnating composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the composition. Preservatives are preferably employed in amounts ranging from 0.01% to 2% by weight of the composition.

Compositions of the present invention may further include herbal extracts. Illustrative extracts include Roman Chamomile, Green Tea, Scullcap, Nettle Root, Swertia Japonica, Fennel and Aloe Vera extracts. Amount of each of the extracts may range from about 0.001 to about 1%, preferably from about 0.01 to about 0.5%, optimally from about 0.05 to about 0.2% by weight of a composition.

Minor adjunct ingredients may also be present in the compositions. Among these may be vitamins such as Vitamin E Acetate, Vitamin C, Vitamin A Palmitate, Panthenol and any of the Vitamin B complexes. Anti-irritant agents may also be present including those of steviosides, alpha-bisabolol and glycyhrizzinate salts, each vitamin or anti-irritant agent being present in amounts ranging from about 0.001 to about 1.0%, preferably from about 0.01 to about 0.3% by weight of the composition.

Emulsifiers may also be incorporated into compositions of this invention. These emulsifiers may be anionic, nonionic, cationic, amphoteric and combinations thereof. Useful non-ionic type emulsifiers include the $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic emulsifiers. Particularly preferred as the emulsifier is a hydrogenated castor wax alkoxylated with 40 moles ethylene oxide, available commercially as Cremophore RH-40®.

Mild emulsifiers of the anionic and amphoteric type may also be employed. Particularly preferred anionic examples include lauroamphoacetate salts and sarcosinate salts. Preferred amphoterics include cocamidopropylbetaine and dimethylbetaine.

Amounts of the emulsifiers may range from about 0.05 to about 20%, preferably from about 0.1 to about 5%, optimally from about 0.5 to about 0.8% by weight.

Low pH systems containing fatty acid ($C_{10}$–$C_{22}$ alkyl) groups such as lauroamphoacetates have been found to emit foul odors. Although not wishing to be bound by theory, it is believed that hydrolysis of surfactants with fatty acid groups cleave. Malodorous fatty acids are thereby formed. Applicants have found that silicone microemulsions such as dimethiconyl microemulsions effectively inhibit odor formation.

These impregnating compositions of the present invention may involve a range of pH although it is preferred to have a relatively low pH, for instance, a pH from about 2 to about 6.5, preferably from about 2.5 to about 4.5.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLES 1–8

Table I provides a listing of formulations which are suitable for impregnation into a cellulosic substrate forming a towelette. The pH of the resulting composition solutions range from about 2.8 to about 4.0.

TABLE I

| INGREDIENT | EXAMPLE (WEIGHT %) | | | | | | | |
|---|---|---|---|---|---|---|---|---|
| | 1 | 2 | 3 | 4 | 5 | 6 | 7 | 8 |
| Water | To 100 | To 100 | To 100 | To 100 | To 100 | To 100 | To 100 | To 100 |
| Glycolic Acid (70% Active) | 11.40 | — | — | — | 10.90 | 10.90 | 1.10 | — |
| Potassium Lactate | — | 8.00 | — | — | — | 0.50 | — | 4.00 |
| Alpha-Hydroxy-octanoic Acid | — | — | 0.50 | — | 0.50 | — | — | — |
| Glucarolactone | — | — | — | 2.00 | — | — | — | — |
| Ammonia Solution (30% Active) | 3.50 | — | — | — | 3.00 | 3.00 | 0.35 | — |
| Glycerin | 1.00 | 1.00 | 1.00 | 1.00 | 1.00 | 1.00 | 1.00 | 1.00 |
| Dimethiconol Microemulsion (25% active) | 0.75 | 0.75 | 0.75 | 0.75 | 4.00 | 3.00 | 2.00 | 0.10 |
| Disodium Capryl-amphodiacetate | 1.00 | 1.00 | 1.00 | 1.00 | 1.00 | 1.00 | 1.00 | 1.00 |
| Witch Hazel Extract | 0.50 | 0.50 | 0.50 | 0.50 | 0.50 | 0.50 | 0.50 | 0.50 |
| Glydant Plus | 0.20 | 0.20 | 0.20 | 0.20 | 0.20 | 0.20 | 0.20 | 0.20 |
| PEG-40 Hydrogenated Castor Oil | 0.50 | 0.50 | 0.50 | 0.50 | 0.50 | 0.50 | 0.50 | 0.50 |
| Fragrance | 0.15 | 0.15 | 0.15 | 0.15 | 0.15 | 0.15 | 0.15 | 0.15 |
| Hexylene Glycol | 2.00 | 2.00 | 2.00 | 2.00 | 2.00 | 2.00 | 2.00 | 2.00 |
| Vitamin E Acetate | 0.001 | 0.001 | 0.001 | 0.001 | 0.001 | 0.001 | 0.001 | 0.001 |

EXAMPLE 9

A study was conducted to evaluate the effects of silicones and other substances for stability and reducing stickiness in low pH hydroxycarboxylic acid depositing towelette products. Towelettes were impregnated with a formulation substantially similar to Example 1 except that the dimethiconol microemulsion was replaced with materials reported under Table II at the specified usage level. An amount of 4 grams formulation was impregnated into each towelette (1.8 gram weight; 6 inch by 8 inch size). Stability refers to the phase compatibility of the fluid which impregnated the towelettes. Ratings were 'good' for homogeneous fluids, 'fair' for those with only a small amount of top creaming, and 'poor' for significant phase separation. Stickiness was evaluated by a trained evaluator and measured by sensory finger feel.

TABLE II

Effects of Various Materials On Stability and
Stickiness of Low pH Fluids Delivered By Towelettes

| Material | CTFA Name | Usage Level | Stability | Effectiveness on stickiness removal (excellent, very good, good, fair, no effect) |
|---|---|---|---|---|
| Silicones | | | | |
| Dow Corning 2501 | Dimethicone copolyol (wax) | 3% | Good | Fair |
| D/C 2-1788 | Dimethicone emulsion | 3% | Poor | Good |
| D/C 2-1310 | Dimethicone emulsion | 3% | Poor | Good |
| D/C FB-50 | Dimethicone emulsion | 3% | Poor | Good |
| D/C 1664 | Dimethicone emulsion | 3% | Poor | Good |
| D/C 2-1870 | Dimethiconol microemulsion | 3% | Good | Good |
| D/C 2-8739 | Dimethicone microemulsion | 3% | Good | Fair |
| Silwet L-7087 | Organosilicone fluid | 3% | Good | No effect |
| Silwax WS-L | Dimethicone copolyol laurate | 3% | Good | No effect |
| Silube CP-I | Dimethicone copolyol phthalate | 3% | Good | Fair |
| Silwax WS | Organomodified dimethicone copolyol | 3% | Good | Fair |
| Pecosil PS-100 Q | Dimethicone copolyol phosphate | 3% | Good | No effect |
| D/C antifoam 1510 | Dimethicone emulsion | 3% | Poor | Good |
| Others | | | | |
| Hetester PHA | Propylene glycol isoceteth-3 acetate | 3% | Poor | Fair |
| Lubragel Oil | Glyceryl polymethacralate, propylene glyol, PVM/MA | 3% | Good | No effect |
| Glycerox HE | PEG-7 glyceryl cocoate | 3% | Good | No effect |
| HPS-1180 | Polysulfonic acid solution | 3% | Good | No effect |
| | | 10% | Good | No effect |
| Lipopeg 4-L | PEG-8 laurate | 3% | Good | No effect |
| Crodesta F-110 | Sucrose stearate and sucrose distearate | 3% | Fair | No effect |
| SMEC concentrate | OMC emulsion | 3% | Good | No effect |
| Glycerox 767 | PEG 6 capric/caprylic glycerides | 3% | Good | No effect |
| Aqua Keep 10 NF | Sodium polyacrylate (SAP) | 1% | Poor | No effect |
| Arconate HP | Propylene carbonate | 3% | Good | No effect |
| MP diol glycol | 2-Methyl 1,3 propanediol | 3% | Good | No effect |
| | 2-methyl 1,3 pentanediol | 3% | Good | No effect |
| Emulgade CM | Cetearyl isonanoate, ceterth-20, cetearyl alcohol, glycerin, cetyl palmitate | 3% | Good | No effect |

Almost all the non-silicone materials had no beneficial effect on ameliorating stickiness of deposited hydroxycarboxylic acids. Dimethicone emulsions did work well to remove stickiness. However, these emulsions imparted poor stability to the fluid formulations. Only dimethiconal microemulsions retained both good physical stability while also effectively combating stickiness.

The foregoing description and examples illustrate selected embodiments of the present invention. In light thereof variations and modifications will be suggested to one skilled in the art, all of which are within the spirit and purview of this invention.

What is claimed is:

1. A towelette product comprising:
 (a) a water-insoluble substrate;
 (b) a cosmetic composition impregnated into the substrate comprising:
  (i) an alpha- or beta-hydroxycarboxylic acid;
  (ii) a silicone microemulsion formulated into the cosmetic composition as a pre-formed microemulsion ingredient;
  (iii) the composition in water having a pH no higher than about 6.5.

2. The towelette product according to claim 1 wherein the alpha-hydroxycarboxylic acid is selected from the group consisting of glycolic, lactic, hydroxyoctanoic acids and mixtures thereof.

3. The towelette product according to claim 1 wherein pH ranges from about 2.0 to about 6.0.

4. The towelette product according to claim 1 wherein the pH ranges from about 3.5 to about 4.5.

5. The towelette product according to claim 1 wherein silicone microemulsion is a dimethiconol microemulsion.

6. The towelette product according to claim 1 wherein the silicone has a particle size ranging from about 0.01 to about 500 nm.

7. The towelette product according to claim 6 wherein the silicone has a particle size ranging from about 5 to about 50 nm.

8. The towelette product according to claim 1 wherein the hydroxycarboxylic acid is present in an amount from about 0.1 to about 15% by weight of the impregnating vehicle.

9. The towelette product according to claim 1 wherein the microemulsion is present in an amount from about 0.1 to about 20% by weight of the impregnating vehicle.

10. The towelette product according to claim 1 wherein the beta-hydroxycarboxylic acid is salicylic acid.

11. The towelette product according to claim 1 wherein the impregnated composition relative to the substrate is present in an amount from about 20:1 to 1:20 by weight.

12. The towelette product according to claim 1 wherein the impregnated composition is a fluid of viscosity ranging from 0.5 to 100 cps.

13. The towelette product according to claim 1 wherein the cosmetic composition further comprises from about 50 to about 99% by weight of water.

14. A towelette product comprising:
(a) a water-insoluble substrate;
(b) a cosmetic composition impregnated into the substrate comprising:
(i) an alpha- or beta-hydroxycarboxylic acid;
(ii) a silicone microemulsion;
(iii) a surfactant containing a $C_{10}$–$C_{22}$ fatty acid group hydrolizable at low pH; and
(iv) the composition in water having a pH no higher than 6.8.

15. The towelette product according to claim 14 wherein the surfactant is selected from the group consisting of lauroamphoacetate, sarcosinate, cocoamido propyl betaine and surfactant mixtures thereof.

* * * * *